United States Patent
Peyton

(10) Patent No.: US 9,259,187 B2
(45) Date of Patent: Feb. 16, 2016

(54) SYSTEM AND METHOD FOR MONITORING CARDIAC OUTPUT WITH SUBSTANTIALLY IMPROVED ACCURACY AND PRECISION

(71) Applicant: Austin Health, Heidelberg, Victoria (AU)

(72) Inventor: Philip John Peyton, Park Orchards (AU)

(73) Assignee: AUSTIN HEALTH, Heidelberg, Victoria (AU)

( * ) Notice: Subject to any disclaimer, the term of this patent is extended or adjusted under 35 U.S.C. 154(b) by 53 days.

(21) Appl. No.: 14/169,091

(22) Filed: Jan. 30, 2014

(65) Prior Publication Data

US 2014/0243696 A1 Aug. 28, 2014

Related U.S. Application Data

(60) Provisional application No. 61/758,657, filed on Jan. 30, 2013.

(51) Int. Cl.
| | | |
|---|---|---|
| *A61B 18/18* | (2006.01) | |
| *A61B 5/00* | (2006.01) | |
| *A61B 5/029* | (2006.01) | |
| *A61B 5/028* | (2006.01) | |
| *A61B 5/083* | (2006.01) | |
| *A61B 6/03* | (2006.01) | |
| *A61B 6/00* | (2006.01) | |

(Continued)

(52) U.S. Cl.
CPC ............. *A61B 5/7225* (2013.01); *A61B 5/028* (2013.01); *A61B 5/029* (2013.01); *A61B 5/0836* (2013.01); *A61B 5/7221* (2013.01); *A61B 5/053* (2013.01); *A61B 5/055* (2013.01); *A61B 6/03* (2013.01); *A61B 6/503* (2013.01); *A61B 8/065* (2013.01); *A61B 8/12* (2013.01)

(58) Field of Classification Search
CPC ........................................................ A61B 8/06
USPC ........................................................... 600/16
See application file for complete search history.

(56) References Cited

U.S. PATENT DOCUMENTS

| 8,613,707 B2 | 12/2013 | Peyton | |
|---|---|---|---|
| 2008/0287812 A1 * | 11/2008 | Parlikar et al. | 600/485 |

OTHER PUBLICATIONS

Peyton, P.J., "Continuous Minimally Invasive Peri-operative Monitoring of Cardiac Output by Pulmonary Capnotracking: Comparison with Thermodilution and Transesophageal Echocardiography," International Journal of Clinical Monitoring and Computing, Apr. 2012, 26 (2), pp. 121-132.

(Continued)

*Primary Examiner* — Nicole F Lavert
(74) *Attorney, Agent, or Firm* — Nixion Peabody LLP; Joseph Bach, Esq.

(57) ABSTRACT

A computerized method for monitoring cardiac output of a subject by a processor executing the method, the method comprising the steps of:
 determining first values of cardiac output of the subject for a first period of time using respective different cardiac output measurement methods having respective first measurement errors; and
 combining the determined first values of cardiac output to determine a second value of cardiac output of the subject for the first period of time, such that the second value of cardiac output has a second measurement error that is less than any of the first measurement errors; and
 at least one of storing, outputting, and displaying data representing the determined second value of cardiac output of the subject.

20 Claims, 11 Drawing Sheets

(51) Int. Cl.
  *A61B 8/06* (2006.01)
  *A61B 8/12* (2006.01)
  *A61B 5/053* (2006.01)
  *A61B 5/055* (2006.01)

(56) References Cited

OTHER PUBLICATIONS

Peyton, P.J., et al. "Minimally Invasive Measurement of Cardiac Output During Surgery and Critical Care: A Meta-analysis of Accuracy and Precision", Anesthesiology, Nov. 2010, 113(5), pp. 1220-1235. Erratum in Anesthesiology, Apr. 2012, 116(4), pp. 973.

Critchley, L.A.H, et al., "A Meta-Analysis of Studies Using Bias and Precision Statistics to Compare Cardiac Output Measurement Techniques," Journal of Clinical Monitoring and Computing, Feb. 1999, 15(2), pp. 85-91.

Bland, J.M., et al., "Statistical Methods for Assessing Agreement Between Two Methods of Clinical Measurement," Lancet, Feb. 1986, 1(8476), pp. 307-310.

Botero, M., "Measurement of Cardiac Output Before and After Cardiopulmonary Bypass: Comparison Among Aortic Transit-Time Ultrasound, Thermodilution, and Noninvasive Partial CO2 Rebreathing," Journal of Cardiothoracic and Vascular Anesthesia, Oct. 2004, 18(5), pp. 563-572.

Peyton, P.J., et al., "Reproducibility of Cardiac Output Measurement by the Nitrous Oxide Rebreathing Technique," Journal of Clinical Monitoring and Computing, Aug. 2009, 23(4), pp. 233-236.

\* cited by examiner

| Method (component) | $\dot{Q}t_{CCO}$ | $\dot{Q}t_{CO_2}$ | $\dot{Q}t_{FT}$ |
|---|---|---|---|
| Mean bias (L/min) | 0.1 | -0.3 | 0.0 |
| Precision (L/min) | 1.5 | 1.3 | 2.5 |
| Percentage error (%) | 51.3 | 42.2 | 82.8 |
| ICC | 0.88 | 0.94 | 0.62 |

| Method (Hybrid) | $\dot{Q}t_{CO_2/CCO}$ | $\dot{Q}t_{CO_2/FT}$ |
|---|---|---|
| Mean bias (L/min) | -0.1 | -0.2 |
| Precision (L/min) | 0.9 | 1.4 |
| Percentage error (%) | 31.3 | 47.5 |
| ICC | 0.96 | 0.89 |

SYSTEM AND METHOD FOR MONITORING CARDIAC OUTPUT WITH SUBSTANTIALLY IMPROVED ACCURACY AND PRECISION

RELATED APPLICATION

This application claims priority from U.S. Provisional Application Ser. No. 61/758,657, filed on Jan. 30, 2013, the disclosure of which is incorporated herein by reference in its entirety.

TECHNICAL FIELD

The present invention relates to a method and system for monitoring the cardiac output of a subject.

BACKGROUND

Cardiac output (pulmonary blood flow) is the rate at which blood is pumped by the heart to the body. Along with the blood pressure, it fundamentally reflects the degree of cardiovascular stability and the adequacy of perfusion of vital organs. Knowledge of the cardiac output will not itself provide a diagnosis of a patient's condition, but can provide information useful in making a diagnosis.

Continuous monitoring of cardiac output is still not performed routinely during anaesthesia and critical care due to the absence of a convenient, safe, non-invasive and accurate and precise method. The established techniques for measuring cardiac output, such as pulmonary thermodilution via a pulmonary artery catheter, are invasive and associated with occasional but serious complications, such as pulmonary artery rupture, and/or are time consuming and heavily operator dependent, as in the case of Doppler echocardiography. Improvements in this field are taking place, such as the development of pulse contour techniques, trans-pulmonary thermodilution, trans-thoracic bio-impedance and derived devices, and methods using pulmonary uptake of inert gases such as nitrous oxide, but these all have limitations, such as poor accuracy under clinical conditions, the need for repeated calibration, invasive central or peripheral cannulation, and/or are simply unsuitable for patients during surgery and critical care who are intubated or ventilated.

Techniques based on the differential Fick principle, such as partial $CO_2$ rebreathing (NICO, Respironics, USA), are among the oldest methods used for cardiac output measurement, and are attractive because of their potentially non-invasive nature. As described in U.S. patent application Ser. No. 12/743,224 and in Peyton P., *Continuous Minimally Invasive Peri-operative Monitoring of Cardiac Output by Pulmonary Capnotracking: Comparison with Thermodilution and Transesophageal Echocardiography*, J. Clin. Monit. Comput. 2012; 26 (2): 121-32, the inventor has recently developed a technique based on measurement of the rate of gas uptake or elimination of $CO_2$ ($\dot{V}_{CO_2}$) by the lungs, referred to herein as the Capnotracking method. The method utilises the differential Fick principle for calibration and an equation relating subsequent changes in $\dot{V}_{CO_2}$ and cardiac output ($\dot{Q}t$) to provide an automated, non-invasive, breath-by-breath cardiac output measurement method and system which is suitable for routine use in ventilated patients undergoing general anaesthesia or in intensive care. The accuracy and precision of this technique in patients undergoing major surgery and critical care is similar to that achieved by other available methods across a wide range of haemodynamic states, as described in Peyton P, and Chong S W., *Minimally Invasive Measurement of Cardiac Output During Surgery and Critical Care: A Meta-analysis of Accuracy and Precision: Erratum*, Anesthesiology, 2012; 116: 972-3 ("Peyton and Chong").

Methods based on a measured variable such as cardiac output in patients suffer from imperfect accuracy and precision of measurement, the sources of error including systematic bias, and both inter-patient and intra-patient factors. The systematic inaccuracy of methods such as the Capnotracking method arises from physiological or physical factors associated with the underlying principles of the measurement of cardiac output, and of the associated input variables. Inter-patient factors include physiological or physical factors contributing to non-linearity of the method in response to the cardiac output. Intra-patient factors include random variability in the measurement of input variables, and of their association to the cardiac output, and include non-linearity of the method in response to changes in cardiac output, which also contribute to lack of reproducibility of measurement. In general, intra-patient variability is less than inter-patient variability for most methods, resulting in more reliable tracking of changes in cardiac output than their precision in measurement of cardiac output across a wide range of patients and haemodynamic states.

When investigating the precision of a given ("test") method in measurement of cardiac output in a population of patients, comparison is usually made with an accepted clinical standard, such as bolus thermodilution. The widely quoted criterion for acceptability of precision of a method for measurement of cardiac output, using thermodilution as the reference method, was defined in Critchley L A H, and Critchley J A: *A Meta-Analysis of Studies Using Bias and Precision Statistics to Compare Cardiac Output Measurement Techniques*, J. Clin. Monit. Comput. 1999; 15: 85-91 ("Critchley and Critchley"). Based on the standard mathematics of error analysis, the error e in agreement between thermodilution and the test method is given by:

$$e = \sqrt{e_{Td}^2 + e_t^2} \qquad \text{Equation 1}$$

where $e_{Td}$ is the error in measurement of cardiac output by thermodilution, and $e_t$ is the error in measurement of cardiac output by the test method. Assuming that both thermodilution and the test method have precision in agreement with the true cardiac output (quantitated as the "limits of agreement", equal to +/−twice the coefficient of variation, within which bounds 95% of measurements are expected to lie as described in Bland J M, Altman D G: *Statistical methods for assessing agreement between two methods of clinical measurement*, Lancet 1986; i: 307-10 ("Bland and Altman")) of +/−20%, the precision of agreement of a test method with thermodilution from Equation 1 is +/−28.3%. Approximating this, Critchley and Critchley recommended that +/−30% represents acceptable precision of agreement with thermodilution by a method for measurement of cardiac output.

Comprehensive review of the published literature in the field over a 10 year period has shown that the precision of agreement with thermodilution being achieved by a wide range of currently available methodologies adapted for use in the peri-operative and critical care setting is much wider (i.e., worse) than this. For example, the precision of pulse contour techniques, oesophageal Doppler, trans-thoracic bioimpedance and the partial $CO_2$ rebreathing methods are all between +/−40 to 45% relative to the accompanying thermodilution measurement, as described in Peyton and Chong. The authors could find no evidence from the studies reviewed that this level of precision was improving with time over the 10 year review period. This relatively poor consistency of agreement with the reference method can be in part attributed to a possibly poorer precision of cardiac output measurement by thermodilution than assumed by Critchley and Critchley (see Botero M, Kirby D, Lobato E B, Staples E D, Gravenstein N, Botero M, Kirby D, Lobato E B, Staples E D, Gravenstein N: *Measurement of cardiac output before and after cardiopulmonary bypass: Comparison among aortic transit-time ultrasound, thermodilution, and noninvasive partial $CO_2$ rebreathing*, J. Cardiothorac. Vasc. Anesth. 2004; 18: 563-72 ("Botero"). Nevertheless, this still represents significantly worse limits of agreement in measurement of the true cardiac output by all techniques than is stipulated as acceptable by these authorities.

In view of the above, there remains a need to find a means for achieving substantially better precision of measurement of cardiac output by techniques adapted for use in peri-operative and critical care patients, so as to prevent misleading data provoking inappropriate clinical decision making, and so as to allow consistent improvements in patient care and clinical outcomes to be obtained from more widespread use of advanced haemodynamic monitoring.

It is desired, therefore, to provide a computerised method and system for monitoring cardiac output of a subject that alleviate one or more difficulties of the prior art, or that at least provide a useful alternative.

SUMMARY

In accordance with the present invention, there is provided a computerized method for monitoring cardiac output of a subject by a processor executing the method, the method comprising the steps of:

determining first values of cardiac output of the subject for a first period of time using respective different cardiac output measurement methods having respective first measurement errors; and combining the determined first values of cardiac output to determine a second value of cardiac output of the subject for the first period of time, such that the second value of cardiac output has a second measurement error that is less than any of the first measurement errors.

The method may include at least one of storing, outputting, and displaying a signal or data representing the determined second value of cardiac output of the subject.

In some embodiments, the second value of cardiac output is generated as a weighted sum of the first values of cardiac output.

In some embodiments, the weighted sum of the first values is generated using equal weights applied to the first values of cardiac output.

In other embodiments, the weighted sum of the first values is generated using different weights applied to the first values of cardiac output.

In some embodiments, the weights are determined dynamically during monitoring of the cardiac output of the subject.

In some embodiments, the method further comprises the steps of:

generating, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and using the generated weights to determine a further weight to be applied to at least one determined value of the at least one of the other cardiac output measurement methods when the selected cardiac output measurement method is not available.

In some embodiments, the method further comprises the steps of:

determining one or more further first values of cardiac output of the subject for a second period of time using all but the selected cardiac output measurement method, respectively; and combining the determined further first values of cardiac output to determine a further second value of cardiac output of the subject for the second period of time, including applying the further weight to at least one determined value of the at least one of the other cardiac output measurement methods to improve the consistency of the determined further second value of cardiac output for the second period of time with the determined second value of cardiac output of the subject for the first period of time.

In some embodiments, said determining includes determining only two first values of cardiac output of the subject for the first period of time using only two respective different cardiac output measurement methods having respective first measurement errors.

In some embodiments, the method includes repeating the steps in a cyclic manner to provide continuous or substantially continuous monitoring of the cardiac output of the subject.

The present invention also provides a tangible computer-readable storage medium having stored thereon computer-executable instructions that, when executed by at least one processor of a computer system, cause the at least one processor to execute the method of any one of the above methods.

The present invention also provides a system for monitoring cardiac output of a subject, the system being configured to execute the method of at least one of the above methods.

The present invention also provides a system for monitoring cardiac output of a subject, the system comprising:

a cardiac output measurement component that determines first values of cardiac output of the subject for a first period of time using respective different cardiac output measurement methods having respective first measurement errors; and a cardiac output measurement combining component in communication with the at least one cardiac output measurement component and that combines the determined first values of cardiac output to determine a second value of cardiac output of the subject for the first period of time, such that the second value of cardiac output has a second measurement error that is less than any of the first measurement errors.

The cardiac output measurement combining component may store, output, and/or display data representing the determined second value of cardiac output of the subject.

In some embodiments, the cardiac output measurement combining component generates the second value of cardiac output as a weighted sum of the first values of cardiac output.

In some embodiments, the cardiac output measurement combining component generates, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and the cardiac output measurement combining component uses the generated weights to determine a further weight to be applied to at least one determined value of the at least one of the other cardiac output measurement methods when the selected cardiac output measurement method is not available.

In some embodiments, the cardiac output measurement combining component determines one or more further first values of cardiac output of the subject for a second period of time using all but the selected cardiac output measurement method, respectively; and combines the determined further first values of cardiac output to determine a further second value of cardiac output of the subject for the second period of time, and applies the further weight to at least one determined value of the at least one of the other cardiac output measurement methods to improve the consistency of the determined further second value of cardiac output for the second period of time with the determined second value of cardiac output of the subject for the first period of time.

BRIEF DESCRIPTION OF THE DRAWINGS

Some embodiments of the invention are hereinafter described, by way of example only, with reference to the accompanying drawings, in which:

FIG. 5 shows data obtained from Botero showing bias and 95% limits of agreement (LoA) for each method studied relative to their gold standard reference method (ultrasonic transit time flow probe on the aorta), and the Hybrid measurement calculated from raw data extracted from their figures.

DETAILED DESCRIPTION

Described herein is a method for monitoring cardiac output ($\dot{Q}t$) or cardiac index (i.e., $\dot{Q}t$ divided by body surface area, BSA) or other variable derived from measured cardiac output. In the described method, which is referred to herein as "the Hybrid method", cardiac output is measured simultaneously, or nearly simultaneously, by two or more (N) different methods of measurement. The resulting measurements are then combined according to the following formula:

$$\dot{Q}_{tH} = \frac{\sum_{i=1}^{i=N} \alpha_i \cdot \dot{Q}_{ti}}{\sum_{i=1}^{i=N} \alpha_i} \qquad \text{Equation 2}$$

where $\dot{Q}t_H$ is the cardiac output calculated by the Hybrid method, and $\dot{Q}_{ti}$ is a previous (usually the most recent) cardiac output measurement made by one of the N methods i, and $\alpha_i$ is the corresponding weighting coefficient for the measurement made by method i.

Expected Improvement in Precision of Measurement of Cardiac Output

Figure 1:
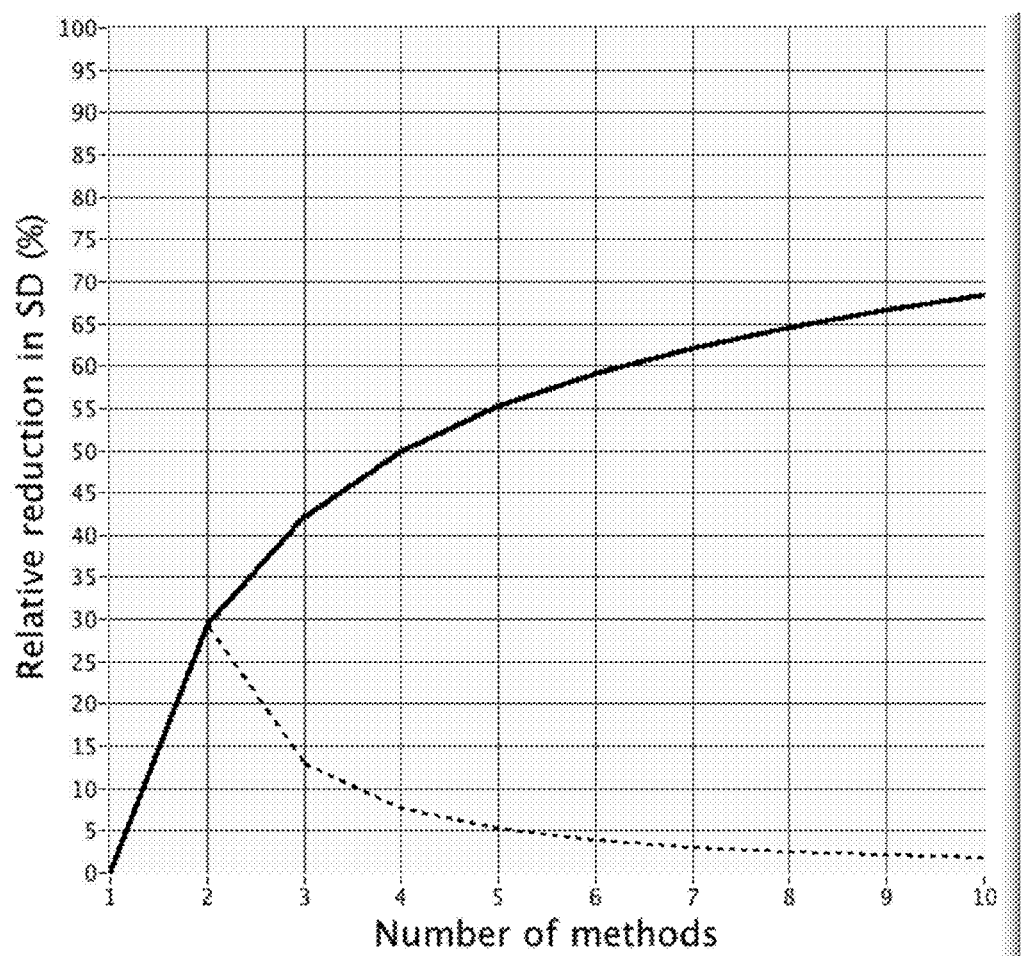
FIG. 1 shows the expected reduction in standard deviation (∂SD) of measurement of cardiac output $\dot{Q}t_H$ from Equation 2, where up to 10 methods are included and all are equally weighted. The heavy line shows the reduction relative to that seen with only one method used. An idealised model is assumed, where the precision of each method in the measurement of cardiac output is equal, the distribution of measurements by each method follows a Gaussian (normal) distribution, and the relationship between the measurements made by the various methods is entirely random (i.e., the sources of error for the different methods are uncorrelated). The relationship is described by Equation 4. The broken line shows the expected reduction in the standard deviation of measurement of cardiac output $\dot{Q}t_H$ from Equation 2 resulting from the addition of each further method, relative to that seen without that addition. It can be seen that the greatest reduction is obtained from the addition of a second method, with progressively reducing additional benefit with each further measurement method incorporated into the Hybrid cardiac output method.

In an idealised model where the precision of each method of cardiac output measurement is equal, the measured cardiac output values are statistically distributed according to a Gaussian (normal) distribution, and the variations between the measurements made by the various methods are entirely random and uncorrelated, then the reduction in standard deviation of measurement of cardiac output ∂SD expected with the addition of each further method to that of method A, as in equation 2, is given by:

$$\partial SD = 1 - 1/\sqrt{N} \qquad \text{Equation 3}$$

where N is the number of measurement methods employed, assuming all methods are equally weighted. FIG. 1 (heavy line) shows this plotted graphically.

In its simplest embodiment, the Hybrid cardiac output value is the average of the cardiac output values measured by only two methods A and B, so that:

$$\dot{Q}t_H = \frac{\alpha \cdot \dot{Q}t_A + \beta \cdot \dot{Q}t_B}{2} \qquad \text{Equation 4}$$

where $$\alpha + \beta = 2$$

Relative to the accuracy and precision of measurement of cardiac output by any single method A, the improvement in accuracy and precision obtained from the Hybrid method is greatest from the addition of measurement by a second method B. Each further additional method can be expected to produce further improvement in accuracy and precision of measurement by the Hybrid method, but at the expense of increased complexity and cost associated with the practical conduct of each measurement method. For each additional method involved, this typically involves one or more of: (i) additional deployment of measurement devices to the patient care environment, (ii) application of the device to the patient via an interface that may involve (iii) minimally—or non-invasive devices such as surface electrodes, probes or transducers, or (iv) invasive cannulation, and (v) collection, calculation, display, assimilation and scrutiny of the resulting data.

FIG. 1 (broken line) shows the relative reduction in the standard deviation of cardiac output measurement (as given by Equation 3) expected with the addition of each further cardiac output measurement method to the calculation of $\dot{Q}t_H$ by Equation 2 using any given number of additional methods (up to 9), where the precision of each method is the same, and all the measurements are equally weighted. It can be seen that the greatest reduction is obtained from the addition of a second method, with progressively reducing additional benefit with each further cardiac output measurement method incorporated into the Hybrid cardiac output method.

In view of the above, the embodiments described hereinbelow use only two cardiac output measurement methods, as described by equation 4, which likely represents the most economical and practical embodiments of the Hybrid method. However, it will be apparent to those skilled in the art that more generally any number of measurement methods can be used and combined as described herein to provide further reductions in standard deviation.

Figure 2:
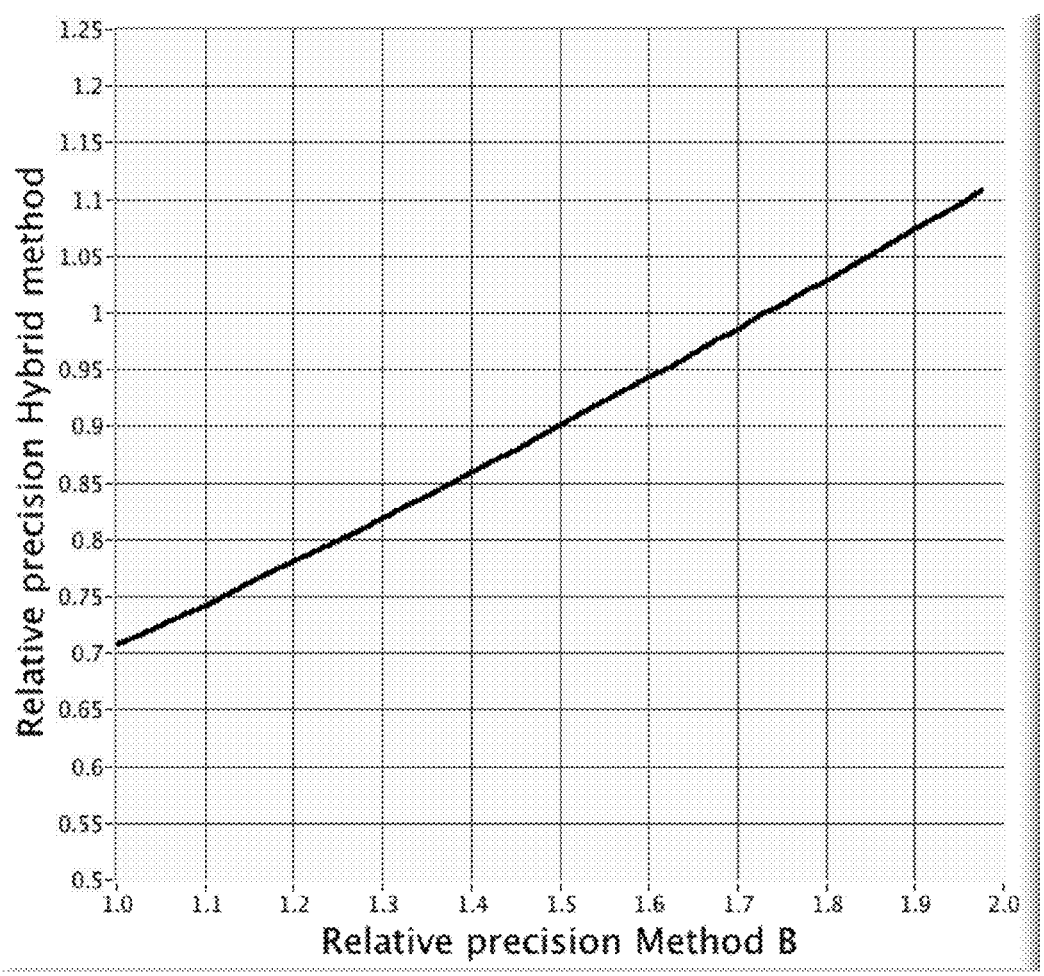
FIG. 2 shows the effect of worsening precision of Method B relative to that of Method A on the precision of the Hybrid cardiac output $\dot{Q}t_H$ obtained using Equation 5. The precision of $\dot{Q}t_H$ remains better than that of Method A until the precision of Method B is 1.75 times worse than that of Method A. This represents a very poor level of precision for Method B (see below), and suggests that the Hybrid method will provide precision superior to that of a single method unless an extremely unreliable method is used as Method B.

The reduction in standard deviation of measurement of cardiac output expected with the addition of a second measurement method B to that of measurement method A, in accordance with Equation 4, depends on the relative precision of each component method. From Equation 3 and FIG. 1, this reduction is expected to be approximately 30% where the precision of the second method 'Method B' is the same as that of 'Method A'.

Where the precision of Method B is poorer than that of Method A, the reduction in standard deviation of measurement of cardiac output $\dot{Q}t_H$ using Equation 4 is expected to be less than the reduction predicted by Equation 3. Moreover, use of a Method B with very poor precision may potentially worsen the precision of $\dot{Q}t_H$ obtained using Equation 4, relative to that given by Method A alone. For example, FIG. 2 shows the effect of worsening the precision of Method B relative to that of Method A on the precision of the Hybrid cardiac output $\dot{Q}t_H$ obtained using Equation 4. FIG. 2 shows that the precision of $\dot{Q}t_H$ remains better than that of Method A until the precision of Method B is 1.75 times worse than that of Method A. This represents a very poor level of precision for Method B and approximates the worst degrees of imprecision recorded among studies comparing the accuracy and precision of measurement of cardiac output with thermodilution as the reference standard (see Peyton and Chong). This suggests that the Hybrid method described herein will provide precision superior to that of a single method using any combinations of the generic methods available in current practice, unless an extremely unreliable method is used as the second Method B.

Accuracy and Reproducibility of Hybrid Cardiac Output Measurement

Any improvement in the precision of measurement will also produce improvement in the mean bias (accuracy) relative to the true cardiac output. Where two component methods suffer from significant systematic bias but in opposite directions, the Hybrid method can be expected to produce a substantial reduction in bias.

One technique for obtaining a more precise and accurate measurement of a physiological parameters such as cardiac output is to make repeated measurements closely associated in time, and average the measured values, and it has been suggested that this should be routine practice for some technologies in the field (see Peyton P, Bailey M, and Thompson B., *Reproducibility of cardiac output measurement by the nitrous oxide rebreathing technique*, J. Clin. Monit. Comput. 2009; 23: 233-6. 10.1007/s10877-009-9187-7). Improvement in the precision of measurement is reflected in better reproducibility of measurement, and will obviate some or all of the need for repeated measurements by component technologies.

Choice of Component Methods for Hybrid Cardiac Output

To maximise the precision of Hybrid method, the component cardiac output measurement methods chosen for the calculation of $\dot{Q}t_H$ from Equations 2 or 4 should not share common sources of error in the measurement of their raw input data, and should not be subject to mathematical coupling in the derivation of their output measurements. This condition is best obtained by choosing methods or devices from two or more of the different classes of cardiac output measurement technologies. These different classes include, but are not restricted to:

(i) arterial blood pressure or plethysmographic waveform-derived estimation of stroke volume and cardiac output, including pulse contour methods and pulse wave transit time;

(ii) methods based on measurement of blood flow in the heart or great vessels by use of ultrasound, including Doppler based measurements as part of echocardiography and use of oesophageal Doppler devices;

(iii) methods based on pulmonary uptake or elimination of gases such as carbon dioxide ($CO_2$) including differential Fick methods such as the partial $CO_2$ rebreathing method, and the Capnotracking method;

(iv) methods based on transthoracic electrical bio-impedance, or related techniques such as electrical velocimetry and bioreactance; and (v) methods based on imaging of the heart or great vessels such as magnetic resonance imaging or radiology using computerised tomography.

These classes of technology for measurement of stroke volume or cardiac output are based on respective different physical and physiological principles, and therefore their measurements of cardiac output are less likely to vary in unison away from the true cardiac output. To put it another way, the sources of error for the different methods that are combined as described herein are ideally not correlated: a stochastic relationship between the measurements obtained from these classes of technology maximises the advantage in precision of measurement obtained from the Hybrid method described herein.

In ideal embodiments, all of the component methods of cardiac output measurement will have documented accuracy and precision of measurement over a wide range of haemodynamic states and cardiac output values which are comparable to the best published data in the field.

To avoid introducing excessive complexity and cost into the Hybrid measurement process, one or more of the component methods may be characterised by minimal interference with the usual conduct of patient care and monitoring. Ideally, such methods will involve few or no peripheral cables or other attachments to the patient apart from those normally required for patient care and be integrated, by means of plug-in modules for example, into the patient monitoring platform to avoid cluttering of the workspace with stand-alone measurement devices. An example of such a method is the Capnotracking method fully integrated into the patient monitoring and ventilation system. Where one of a pair of component methods meets these criteria, the cost and complexity of the Hybrid method for the clinician or carer is no greater than that of the second method itself, while delivering substantially better accuracy and precision of cardiac output measurement than can be achieved by either component method alone.

Determination of Weighting Coefficients for the Component Methods

The choice of weighting coefficients in Equations 2 or 4 may be based on a number of factors reflecting the relative accuracy and precision of each component method. Examples of these factors include, but are not restricted to, the following:

(i) data from investigative studies, case reports, reviews, synthesis or meta-analyses on the accuracy and precision of a component method relative to another reference method or to an estimate of the true cardiac output;

(ii) data from investigative studies, case reports, reviews, synthesis or meta-analyses on the accuracy and precision of a component method relative to another reference method or to an estimate of the true cardiac output, in certain groups of patients or during certain clinical circumstances or scenarios;

(iii) assessment of the accuracy, precision or other index of quality of input data or measurements of raw signals by a component method;

(iv) the elapsed time since a prior calibration measurement of the component method has been made;

(v) the measured cardiac output itself, where one component method is thought to be more accurate or precise within a certain range of haemodynamic states or cardiac output values than the other component method(s);

(vi) the rate of change in measured cardiac output, where one component method is thought to have a faster response time in real-time measurement of changes in cardiac output.

Incorporation of factors such as these, and others, may involve application of feedback loops in the calculation of $\dot{Q}t_H$.

Thus, the weighting coefficients applied to one or more of the component methods can change between patients or can change over time (i.e., can be dynamically generated) within the course of measurement in a given patient. In some embodiments, the weighting coefficients are retrieved from a database and applied automatically.

the Weighting Coefficient as a Transfer Factor T

A coefficient for the cardiac output measurement by a component method can be obtained which applies as, or in place of, the weighting coefficient for that method after ongoing measurements by the other component method(s) have been interrupted or ceased. For example, from Equation 4:

$$\dot{Q}t_H = \frac{\alpha \cdot \dot{Q}t_A + \beta \cdot \dot{Q}t_B}{2} \qquad \text{Equation 4}$$

where $$\alpha + \beta = 2$$

Therefore $$\dot{Q}t_H = \dot{Q}t_A \cdot \frac{1}{2}\left(\alpha + \frac{\beta \cdot \dot{Q}t_B}{\dot{Q}t_A}\right) \qquad \text{Equation 5}$$

$$\frac{1}{2}\left(\alpha + \frac{\beta \cdot \dot{Q}t_B}{\dot{Q}t_A}\right)$$

is the transfer factor T which applies to Method A, and is calculated continuously while ongoing measurements by both Methods A and B are being made. An average, median or other measure of central tendency for the value for T can be calculated, updated and stored periodically or continuously.

When measurement by one or other method (say, in this example Method B) ceases or is interrupted, the stored value of T can be used as, or instead of, the weighting coefficient for ongoing measurements by Method A. This effectively allows Method A to be calibrated by the Hybrid method in that patient for ongoing measurements.

An example of this is the transfer of a patient who has undergone surgery to a high-dependency unit after emergence from anaesthesia and extubation. Monitoring of cardiac output may have been done by the Hybrid method during surgery while the patient was ventilated using a pulse contour device (as Method A) and the Capnotracking method (as Method B). After extubation and transfer to the post-anaesthesia recovery or high-dependency unit, continuing monitoring of cardiac output by the pulse contour method (Method A) alone can continue. The value of T is entered into the monitoring system, by either manual or automated means, and $\dot{Q}t_A$ is consequently modified to give $\dot{Q}t_H$ in the postoperative period from equation 5. This provides a more consistent value of cardiac output than if the result of Method A was used directly without scaling, but of course the result no longer benefits from the stochastic advantage of the Hybrid method in improving the degree of random intra-patient scatter in subsequent cardiac measurement by Method A alone.

A System for Monitoring Cardiac Output by the Hybrid Method

Figure 3:
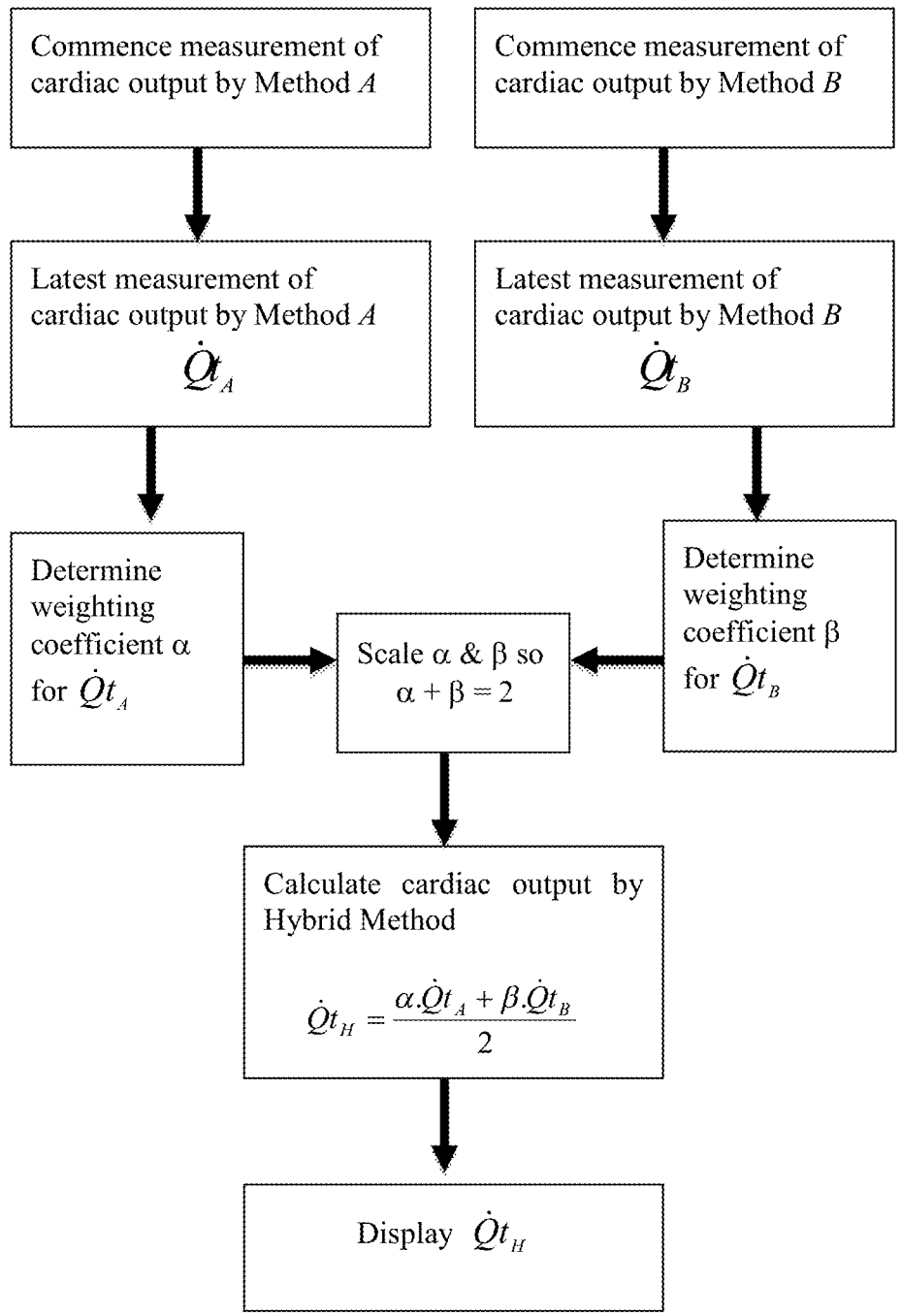
FIG. 3 is a flow diagram of an embodiment of the Hybrid method used to obtain a Hybrid cardiac output measurement on a single, intermittent or continuous basis from two corresponding cardiac output measurement methods.

The Hybrid method can be implemented using any combination of component methods, operating either as stand-alone devices or integrated into the patient monitoring platform. By way of example, FIG. 3 is a flowchart of a process of obtaining the Hybrid cardiac output $\dot{Q}t_H$ using Equation 4 from two component methods A and B providing cardiac output measurements $\dot{Q}t_A$ and $\dot{Q}t_B$.

In some embodiments, following commencement of measurement on either a single, intermittent or continuous basis by either or both of methods A and B, the inputs $\dot{Q}t_A$ and $\dot{Q}t_B$ are previous (usually the most recent and updated) measurements by the respective methods. The values for the inputs $\dot{Q}t_A$ and $\dot{Q}t_B$ are received as data inputs to a computing device, such as exists within the patient monitoring platform, or other related or available computing device. The weighting coefficients $\alpha$ and $\beta$ to be applied are automatically retrieved from a database by the process.

Data representing the Hybrid cardiac output value $\dot{Q}t_H$ from Equation 4 is automatically generated and displayed, and is updated whenever an updated value for either of the inputs $\dot{Q}t_A$ and $\dot{Q}t_B$ becomes available. In some embodiments, data representing a Hybrid cardiac index is generated and displayed, either in addition or instead, optionally along with data representing corresponding values of one or more haemodynamic variables which can be determined once a measurement of cardiac output or index is available. In some embodiments, a cardiac output monitoring system is configured to display an indication of "normal ranges" for cardiac output, cardiac index and other derived haemodynamic variables, and to trigger an alarm to alert the clinician or carer of any deviation outside these ranges.

Figure 7:
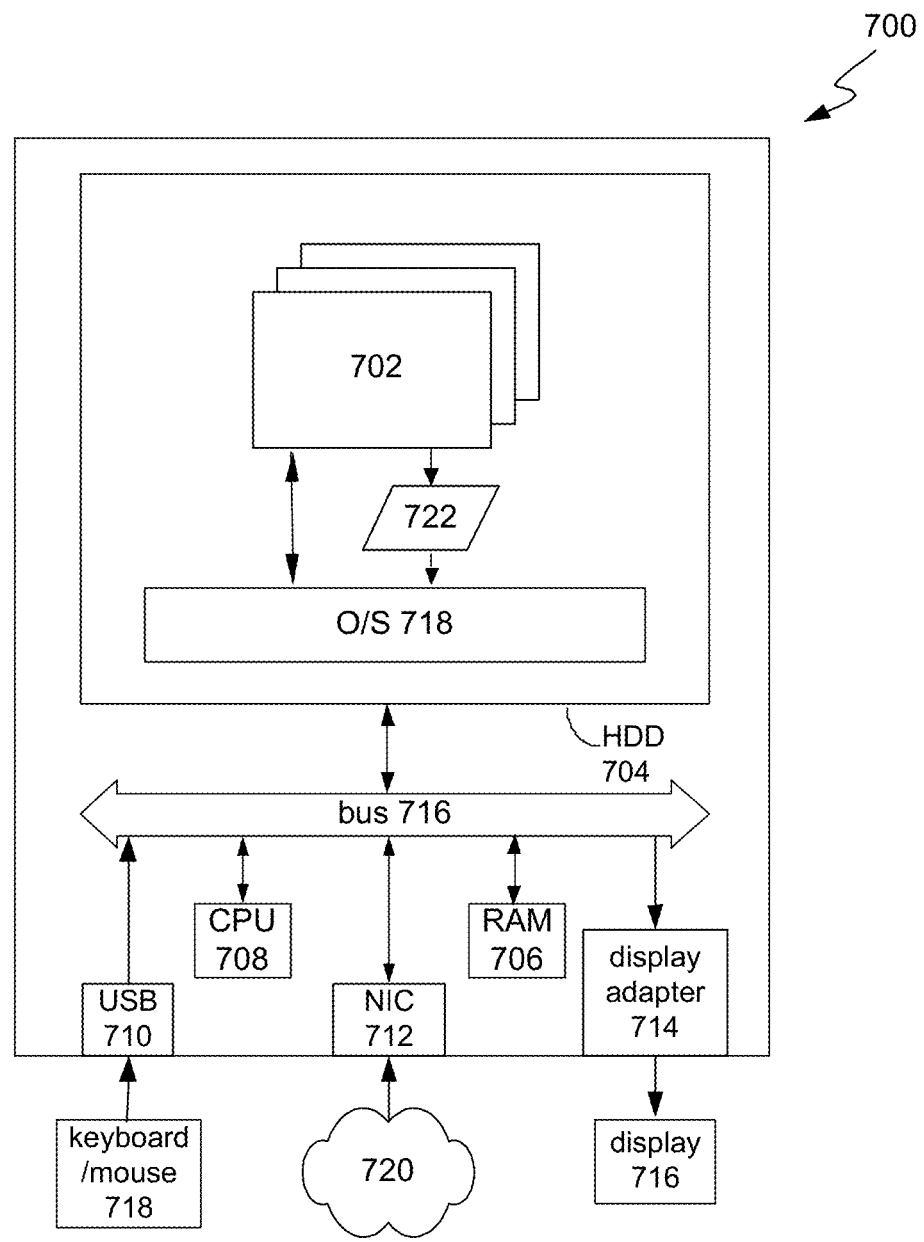
FIG. 7 is a block diagram of an embodiment of a cardiac output monitoring system.

In some embodiments, a cardiac output monitoring system is a standard computer system 700, and the Hybrid cardiac output monitoring method is implemented in software as one or more cardiac output monitoring modules 702 stored on tangible and non-volatile (e.g., solid state or hard disk) storage 704 associated with the computer system, as shown in FIG. 7. The cardiac output monitoring modules 702 may include at least one cardiac output measurement component and a cardiac output measurement combining component that generates a signal or data 722 representing the cardiac output of the subject determined by the Hybrid cardiac output monitoring method.

In some embodiments, the computer system is a component of a patient ventilator. In any case, it will be apparent to those skilled in the art that the various components of the cardiac output monitoring system can be alternatively distributed over a variety of locations and in various combinations, and that in other embodiments at least part of the Hybrid cardiac output monitoring method can alternatively be implemented by one or more dedicated hardware components such as application-specific integrated circuits (ASICs) and/or as configuration data for one or more field-programmable gate arrays (FPGAs), for example.

In the described embodiment, the system 700 includes standard computer components, including random access memory (RAM) 706, at least one processor 708, and external interfaces 710, 712, 714, all interconnected by a bus 716. The external interfaces include universal serial bus (USB) interfaces 710, at least one of which is connected to a keyboard 718 and a pointing device such as a mouse, a network interface connector (NIC) 712 which connects the system 700 to a communications network 720 such as the Internet, and a display adapter 714, which is connected to a display device such as an LCD panel display 716. The system 700 also includes an operating system 718 such as Linux or Microsoft Windows.

Smoothing Functions:

In some embodiments, to reduce the effects of random measurement imprecision on $\dot{Q}t_H$, a moving average of $\dot{Q}t_H$ can optionally be used. This has the effect of delaying the responsiveness of the system to real-time changes in cardiac output, but provides more stable results. Alternatively or additionally, the measurement values provided by each of the component methods $\dot{Q}t_A$, $\dot{Q}t_B$ etc can be individually smoothed prior to their combination. Technical improvements in the measurement of input parameters for the component methods which reduce random measurement imprecision may allow shorter averaging or none at all, thereby improving the real-time responsiveness of the system.

EXAMPLE I

Simulated Data Using a Computer Model.

Figure 4:
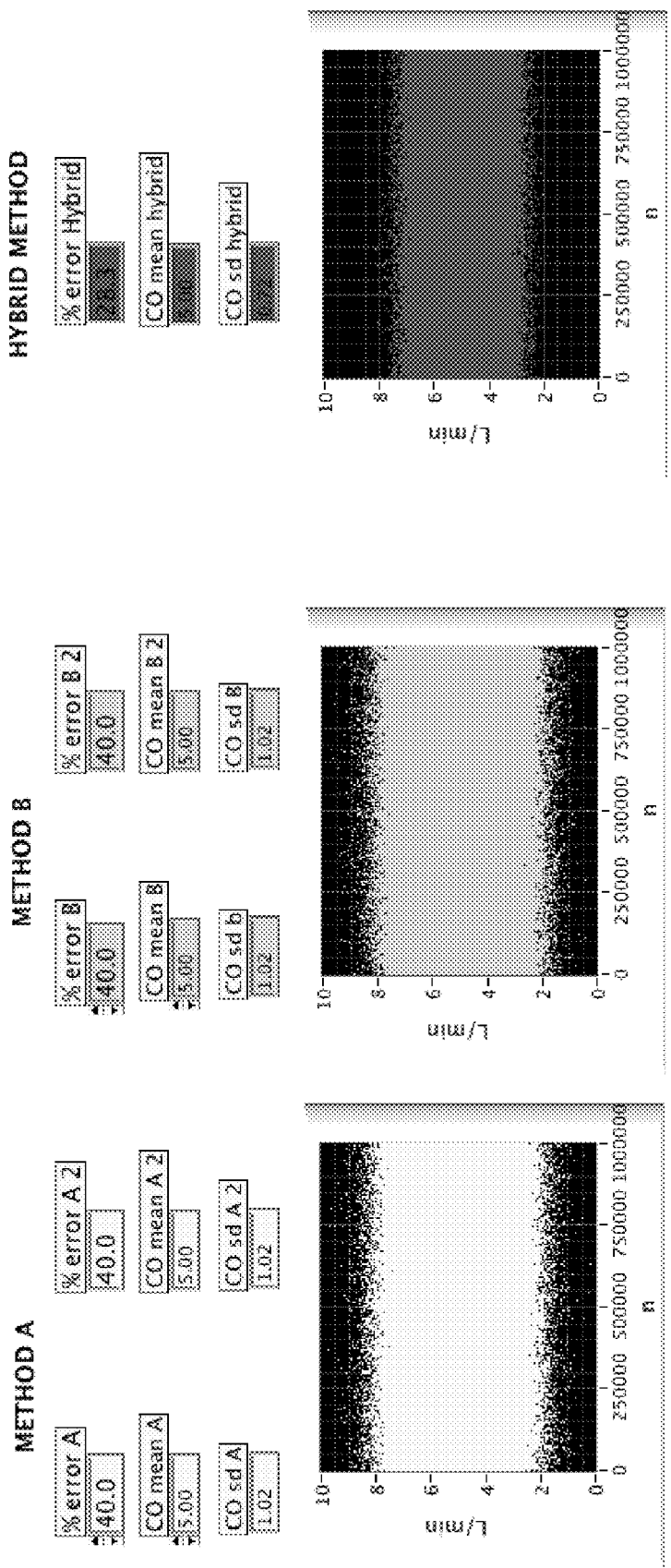
FIG. 4 shows simulated data from an idealised model where the distribution of measurements by each method follows a Gaussian (normal) distribution, and the relationship between the measurements made by the various methods is random. The simulated cardiac output was set at 5 L/min with random variation by a Gaussian white noise generator producing $10^6$ measurements for each of method A and method B, with a precision (one standard deviation) set at 20% of this value for both, giving 95% limits of agreement of +/−40% or +/−2 L/min for each component method. The precision of the calculated Hybrid cardiac output is substantially better, with limits of agreement of +/−28.3%.

Using an idealised Monte Carlo model where the distribution of measurements by each method follows a Gaussian (normal) distribution, and the relationship between the measurements made by the various methods is entirely random (i.e., the sources of error for the respective methods are uncorrelated or at least substantially uncorrelated), the improvement in precision of measurement of cardiac output which accompanies the addition of measurements by a method B to that of method A, as in equation 4, is demonstrated in FIG. 4. The simulated cardiac output was set at 5 L/min with random variation by a Gaussian white noise generator producing $10^6$ measurements for each of method A and method B, with a precision (one standard deviation) set at 20% of this value for both, giving 95% limits of agreement of +/−40% or +/−2 L/min for each component method. The precision of the calculated Hybrid cardiac output (from Equation 4) is substantially better, with 95% limits of agreement of +/−28.3%. The reduction in the standard deviation of the Hybrid measurement ($\partial SD$) follows the formula $\partial SD = 1 - 1/\sqrt{N}$ (Equation 4) where in this case n=2.

EXAMPLE II

Published Data from Botero

Published clinical data from Botero was used to demonstrate the ability of the Hybrid method to produce substantial improvements in the precision of cardiac output measurement using existing component methods which are currently in common clinical use.

In their study, the relative accuracy and precision of three methods of measurement of cardiac output were assessed by comparison with a gold standard. With institutional review board approval, sixty-eight consenting patients undergoing cardiac surgery were cannulated, in accordance with standard clinical practice, with a pulmonary artery catheter capable of providing intermittent bolus and continuous thermodilution measurement of pulmonary blood flow via Vigilance monitor (Baxter Healthcare Corporation, Irvine, Calif., USA), as well as non-invasive measurement of pulmonary blood flow by the partial $CO_2$ rebreathing method using a NICO™ monitor (Novametrix Medical Systems, Wallingford, Conn., USA). For the purposes of the study, the gold standard reference method used was an ultrasonic transit time flow probe (Transonic Systems Inc, Ithaca, N.Y., USA) applied to the ascending aorta prior to cannulation for cardiopulmonary bypass. Contemporaneous measurements were recorded using all four modalities, and the agreement of the three clinical measurement devices with the flow probe was made prior to commencement of and after separation from bypass.

Figure 5A:
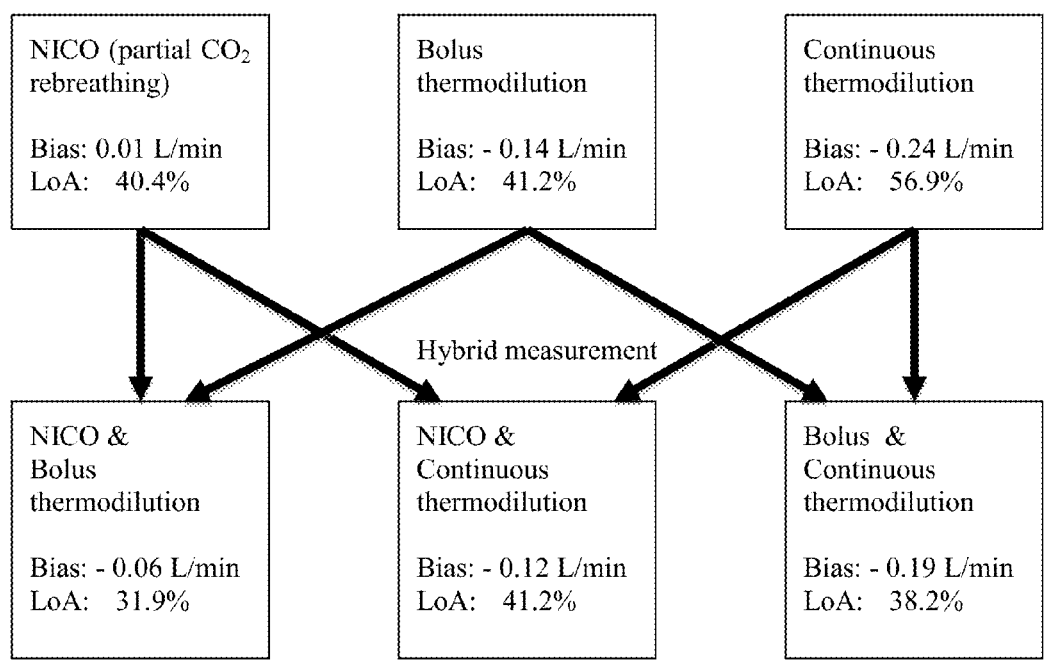
FIG. 5a: Pre-cardiopulmonary bypass measurements.
Figure 5B:
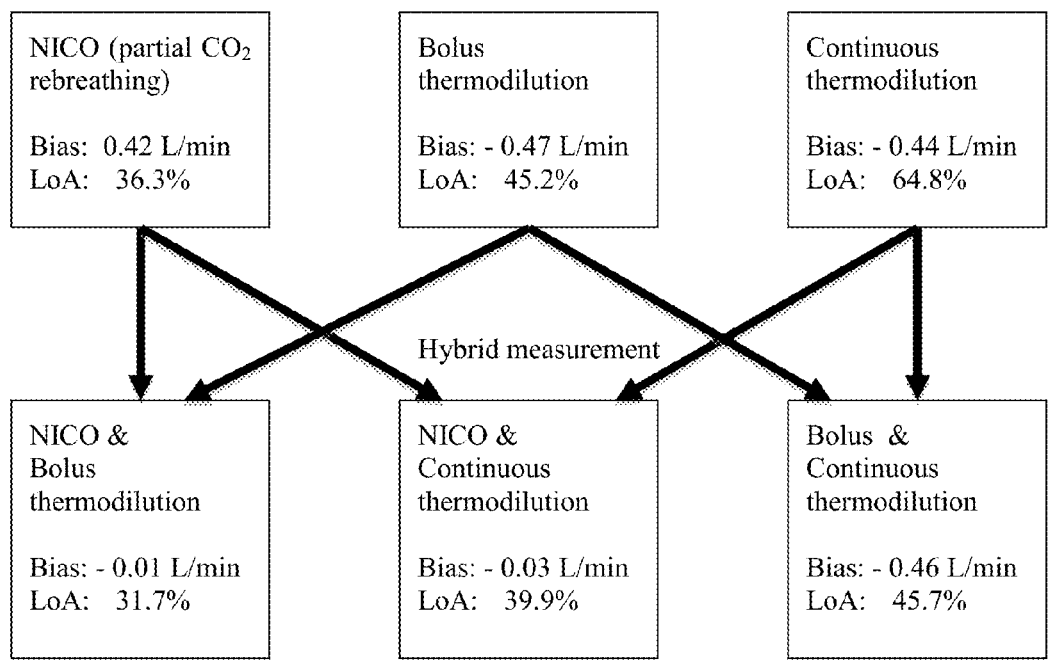
FIG. 5b: Post-cardiopulmonary bypass measurements.

Raw data for measured cardiac output has been calculated from data points extracted from the Bland-Altman agreement plots in their paper. The limits of agreement with the flow probe from these extracted data points are as shown in FIG. 5a (pre-cardiopulmonary bypass measurements) and FIG. 5b (post-cardiopulmonary bypass measurements), along with the Hybrid cardiac output measurements (using Equation 4, with equal weighting applied to both component methods) that can be calculated for the three different combinations of component methods made available from the data.

FIG. 5 shows that, for all the methods tested, the agreement with the invasive gold standard reference method was significantly worse than the threshold for acceptability (+/−30%) recommended by Critchley and Critchley. This was particularly true for Continuous thermodilution, where limits of agreement pre- and post-cardiopulmonary bypass were 56.9% and 64.8% respectively.

However, the Hybrid cardiac output measurements calculated for the three combinations had significantly better agreement with the reference method. For the NICO/bolus thermodilution Hybrid, the limits of agreement closely approached the +/−30% threshold for acceptability (31.9% and 31.7% pre- and post-cardiopulmonary bypass). It should be noted that even for the Hybrid combinations involving the Continuous thermodilution component, the precision of agreement of the Hybrid was not significantly worse than that of the other, more precise, component. Note that bias relative to the reference method was also significantly improved by the Hybrid method in the post-cardiopulmonary bypass measurements.

EXAMPLE III

Published Data from Peyton and Chong

Figure 6:
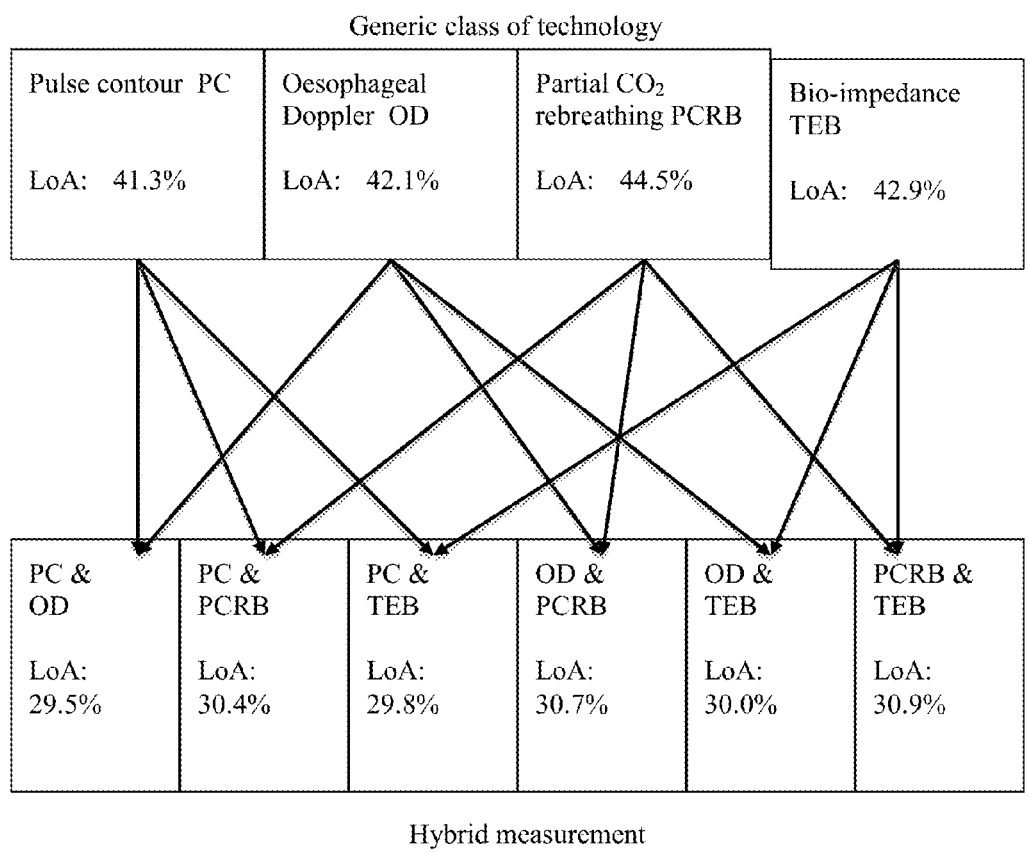
FIG. 6 shows meta-analysis data on the precision of measurement of four generic classes of technology for measurement of cardiac output, from Peyton and Chong, and the precision expected from the Hybrid method using these component methods in various combinations, expressed as 95% limits of agreement (two standard deviations of the difference between paired measurements) with bolus thermodilution.

Data from the published meta-analysis by Peyton and Chong allows an estimate to be made of the expected precision of the Hybrid method using currently available component cardiac output measurement technologies. These authors reviewed published papers from the 10 years 2000-9 and included papers where comparison was made with bolus thermodilution with results presented as bias and precision according to the method of Bland and Altman. FIG. 6 lists the precision these authors found for four generic classes of cardiac output measurement technologies using a pooled weighted meta-analysis of published data on the precision of agreement with bolus thermodilution of four generic classes of technology for measurement of cardiac output, expressed as 95% limits of agreement (two standard deviations of the difference between paired measurements).

Using Monte Carlo modelling as employed in FIG. 4 and FIG. 2, the expected precision of Hybrid measurements obtained from the possible combinations of these four groups were calculated. FIG. 6 shows that the precision expected from the Hybrid method using these component methods was substantially better in all six possible combinations of two methods. For all combinations of currently available generic technology, the Hybrid method achieved precision of agreement with bolus thermodilution that exceeded or closely approached the +/−30% criterion for acceptability stipulated by authorities (see Critchley and Critchley).

EXAMPLE IV

Clinical Study

The Hybrid method was tested by comparing the accuracy and precision of cardiac output measurement relative to simultaneous bolus thermo-dilution measurements (average of 3 bolus measurements on each occasion) via a pulmonary artery catheter, using combinations of three component cardiac output measurement methods.

With approval from the local institutional ethics committee, 30 patients scheduled for either elective cardiac surgery or liver transplantation were studied at the Austin Hospital, Melbourne, Australia.

Pulmonary capnotracking ($QtCO_2$) measurements of cardiac output were combined with either:
(i) continuous thermodilution measurements of cardiac output (QtCCO); or
(ii) Vigeleo/FloTrac pulse contour measurements of cardiac output (QtFT)
to determine corresponding Hybrid values of cardiac output as described herein. The agreement of these Hybrid values with cardiac output measurements by thermodilution was assessed.

Figure 8:
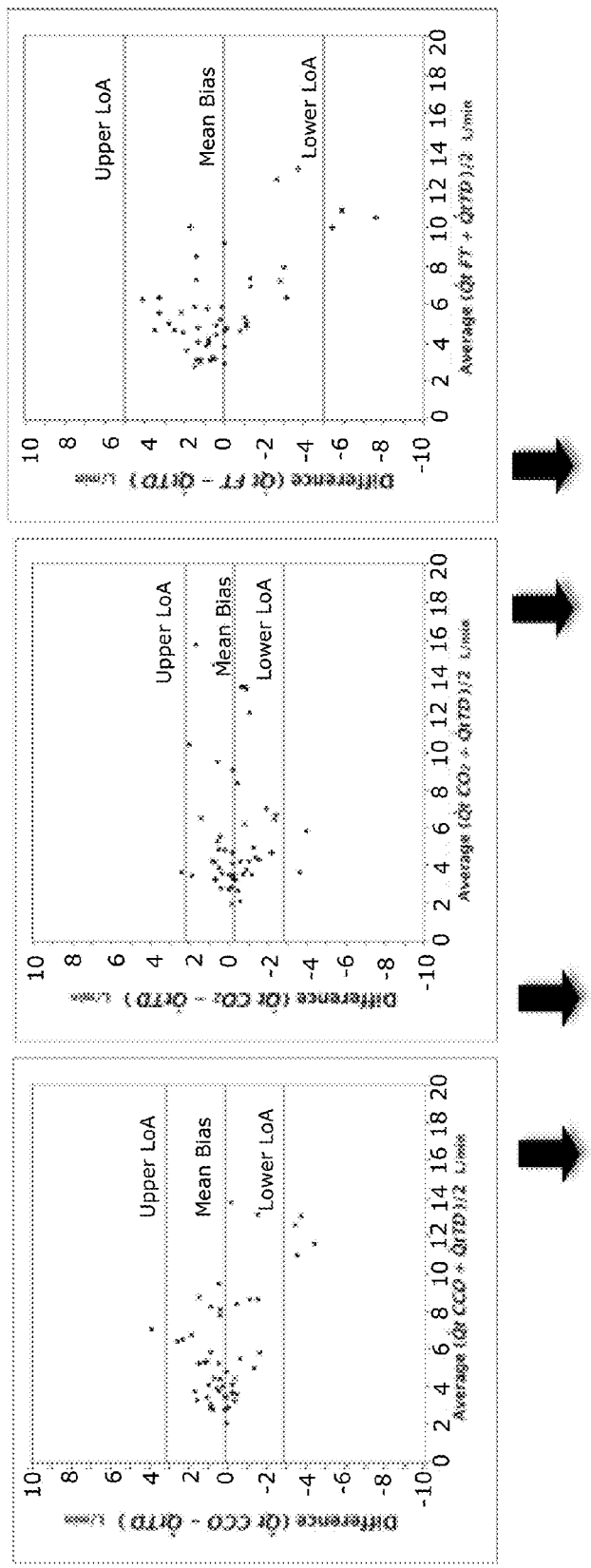
FIG. 8 shows a set of Bland Altman plots representing agreement between bolus thermodilution ($\dot{Q}t_{TD}$) and three further cardiac output measurement methods and Hybrid combinations of those methods. The upper and lower limits of agreement (LoA) and mean bias are shown. The three component methods are the Capnotracking method ($\dot{Q}t_{CO_2}$), continuous thermodilution $\dot{Q}t_{CCO}$, and Vigeleo/FloTrac $\dot{Q}t_{FT}$. The two Hybrid methods shown are $\dot{Q}t_{CO_2/CCO}$, a Hybrid of the Capnotracking and continuous thermodilution methods, and $\dot{Q}t_{CO_2/FT}$, a Hybrid of the Capnotracking and Vigeleo/FloTrac methods.
Figure 8:
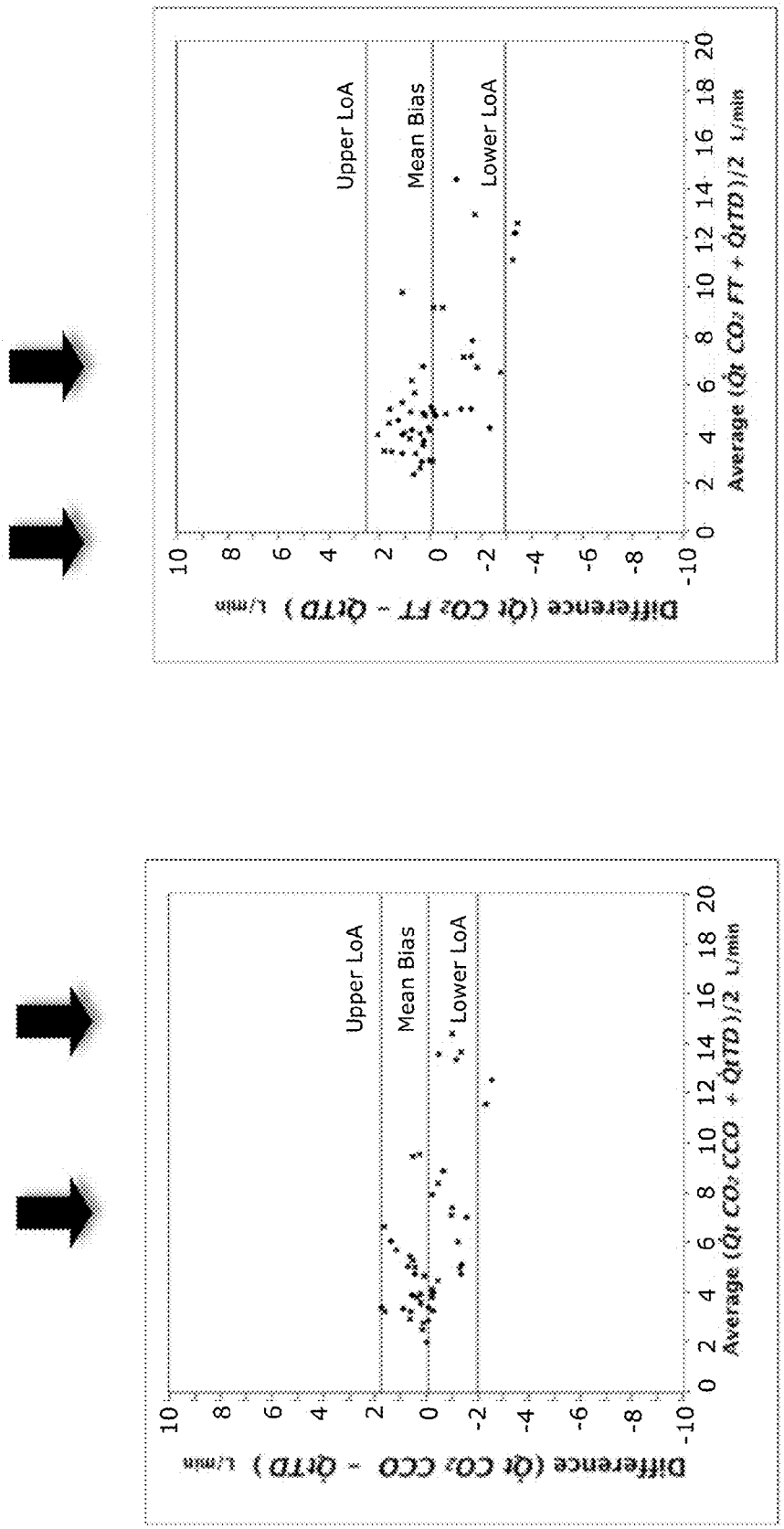

The measurements and assessments were done pre- and post-cardiopulmonary bypass or pre- and post-reperfusion of the donor liver. A total of 50 sets of measurements were collected. Agreement with thermodilution was assessed for the two Hybrid combinations, and compared with that of the component methods alone, using Bland Altman statistics, as shown in FIG. 8.

Figure 9:
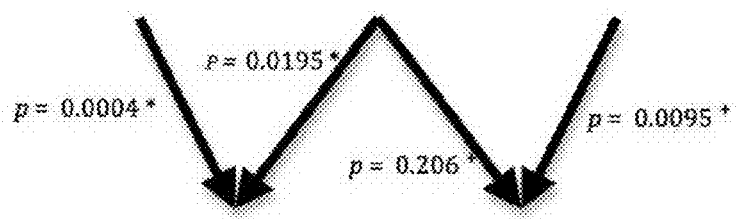
FIG. 9 shows the bias, precision, percentage error, and intraclass correlation coefficient (ICC) for each of the component cardiac output measurement methods of FIG. 8 and for the primary Hybrid combinations, relative to bolus thermodilution ($\dot{Q}t_{TD}$). With regard to the p-values, * represents the F-test, and + Levene's robust test.

For each method and Hybrid combination, the standard deviation and variance of the difference between paired measurements was calculated, along with the percentage error (% error: 2 standard deviations divided by the mean cardiac output), as shown in FIG. 9. The statistical significance of the differences in variances was determined using either the F-test for normally distributed data, or by Levene's robust test for equality of variances, which does not assume normality of data distributions.

Results

Hybridization of $QtCO_2$ (% error 42.2%) and QtCCO (% error 51.3%) achieved significantly better precision (% error 31.3%) than the component methods (p=0.0004 and p=0.0195). Due to the poor inherent precision of QtFT (% error 82.8%), Hybrid combination of QtFT with $QtCO_2$ did not result in better precision than $QtCO_2$ alone.

Conclusion

The Hybrid measurement can approach a percentage error of +/−30% which is recommended as the criterion for acceptability.

Many modifications will be apparent to those skilled in the art without departing from the scope of the present invention.

The invention claimed is:

1. A computerized method for monitoring cardiac output of a subject by a processor executing the method, the method comprising the steps of:
   determining first values of cardiac output of the subject for a first period of time using respective different cardiac output measurement methods having respective first measurement errors whose sources are uncorrelated; and
   combining the determined first values of cardiac output to determine a second value of cardiac output of the subject for the first period of time, such that the second value of cardiac output has a second measurement error that is less than any of the first measurement errors; and at least one of storing, outputting, and displaying data representing the determined second value of cardiac output of the subject.

2. The method of claim 1, wherein the second value of cardiac output is generated as a weighted sum of the first values of cardiac output.

3. The method of claim 2, wherein the weighted sum of the first values is generated using equal weights applied to the first values of cardiac output.

4. The method of claim 2, wherein the weighted sum of the first values is generated using different weights applied to the first values of cardiac output.

5. The method of claim 4, wherein the weights are determined dynamically during monitoring of the cardiac output of the subject.

6. The method of claim 1, further comprising the steps of:
generating, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and
using the generated weights to determine a further weight to be applied to at least one determined value of the at least one of the other cardiac output measurement methods when the selected cardiac output measurement method is not available.

7. The method of claim 6, further comprising the steps of:
determining one or more further first values of cardiac output of the subject for a second period of time using all but the selected cardiac output measurement method, respectively; and
combining the determined further first values of cardiac output to determine a further second value of cardiac output of the subject for the second period of time, including applying the further weight to at least one determined value of the at least one of the other cardiac output measurement methods to improve the consistency of the determined further second value of cardiac output for the second period of time with the determined second value of cardiac output of the subject for the first period of time.

8. The method of claim 2, further comprising the steps of:
generating, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and
using the generated weights to determine a further weight to be applied to at least one determined value of the at least one of the other cardiac output measurement methods when the selected cardiac output measurement method is not available.

9. The method of claim 8, further comprising the steps of:
determining one or more further first values of cardiac output of the subject for a second period of time using all but the selected cardiac output measurement method, respectively; and
combining the determined further first values of cardiac output to determine a further second value of cardiac output of the subject for the second period of time, including applying the further weight to at least one determined value of the at least one of the other cardiac output measurement methods to improve the consistency of the determined further second value of cardiac output for the second period of time with the determined second value of cardiac output of the subject for the first period of time.

10. The method of claim 4, further comprising the steps of:
generating, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and
using the generated weights to determine a further weight to be applied to at least one determined value of the at least one of the other cardiac output measurement methods when the selected cardiac output measurement method is not available.

11. The method of claim 10, further comprising the steps of:
determining one or more further first values of cardiac output of the subject for a second period of time using all but the selected cardiac output measurement method, respectively; and
combining the determined further first values of cardiac output to determine a further second value of cardiac output of the subject for the second period of time, including applying the further weight to at least one determined value of the at least one of the other cardiac output measurement methods to improve the consistency of the determined further second value of cardiac output for the second period of time with the determined second value of cardiac output of the subject for the first period of time.

12. The method of claim 1, wherein said determining includes determining only two first values of cardiac output of the subject for the first period of time using only two respective different cardiac output measurement methods having respective first measurement errors.

13. The method of claim 1, further comprising repeating the steps in a cyclic manner to provide continuous or substantially continuous monitoring of the cardiac output of the subject.

14. The method of claim 2, further comprising repeating the steps in a cyclic manner to provide continuous or substantially continuous monitoring of the cardiac output of the subject.

15. A tangible computer-readable storage medium having stored thereon computer-executable instructions that, when executed by at least one processor of a computer system, cause the at least one processor to execute the method of claim 1.

16. A system for monitoring cardiac output of a subject, the system being configured to execute the method of claim 1.

17. A system for monitoring cardiac output of a subject, the system comprising:
at least one cardiac output measurement component that determines first values of cardiac output of the subject for a first period of time using respective different cardiac output measurement methods having respective first measurement errors whose sources are uncorrelated; and
a cardiac output measurement combining component in communication with the at least one cardiac output measurement component and that combines the determined first values of cardiac output to determine a second value of cardiac output of the subject for the first period of time, such that the second value of cardiac output has a second measurement error that is less than any of the first measurement errors, and that stores, outputs, and/or displays data representing the determined second value of cardiac output of the subject.

18. The system of claim 17, wherein the cardiac output measurement combining component generates the second value of cardiac output as a weighted sum of the first values of cardiac output.

19. The system of claim 17, wherein the cardiac output measurement combining component generates, for a selected one of the cardiac output measurement methods, one or more corresponding weights for respective measurement time periods, the generated weights representing the relationship between the determined values of cardiac output for the selected cardiac output measurement method and corresponding determined values of cardiac output for at least one of the other cardiac output measurement methods; and the cardiac output measurement combining component uses the generated weights to determine a further weight to be applied to at least one determined value of the at least one of the other cardiac output measurement methods when the selected cardiac output measurement method is not available.

20. The system of claim 19, wherein the cardiac output measurement combining component determines one or more further first values of cardiac output of the subject for a second period of time using all but the selected cardiac output measurement method, respectively; and combines the determined further first values of cardiac output to determine a further second value of cardiac output of the subject for the second period of time, and applies the further weight to at least one determined value of the at least one of the other cardiac output measurement methods to improve the consistency of the determined further second value of cardiac output for the second period of time with the determined second value of cardiac output of the subject for the first period of time.

* * * * *